US010384077B2

(12) United States Patent
Benson

(10) Patent No.: US 10,384,077 B2
(45) Date of Patent: Aug. 20, 2019

(54) SECURING A MARKER WIRE

(75) Inventor: Maria Benson, Boylston, MA (US)

(73) Assignee: Hologic Inc., Marlborough, MA (US)

(*) Notice: Subject to any disclaimer, the term of this patent is extended or adjusted under 35 U.S.C. 154(b) by 1741 days.

(21) Appl. No.: 13/083,719

(22) Filed: Apr. 11, 2011

(65) Prior Publication Data

US 2012/0259207 A1 Oct. 11, 2012

(51) Int. Cl.
A61B 5/055 (2006.01)
A61N 5/10 (2006.01)
A61B 19/00 (2006.01)
A61B 8/08 (2006.01)

(52) U.S. Cl.
CPC ............ *A61N 5/1027* (2013.01); *A61B 19/54* (2013.01); *A61B 8/0841* (2013.01); *A61B 2019/5487* (2013.01); *A61N 5/1049* (2013.01)
USPC .......................................... 600/424; 128/899

(58) Field of Classification Search
CPC ....... B65H 2701/31; A61B 5/06; A61B 6/481; A61B 5/055; A61B 2019/2242; A61B 2019/5487; A61B 19/54; A61B 2019/5404; A61B 2019/5408; A61B 2019/5412; A61B 17/162; A61B 17/17; A61B 2090/3987; A61N 5/1027
USPC ............. 403/359.3, 371; 606/167, 184, 185; 600/424, 562, 566, 567; 128/899; 607/116

See application file for complete search history.

(56) References Cited

U.S. PATENT DOCUMENTS

| 2,147,239 | A | * | 2/1939 | Buchanan | 403/371 |
|---|---|---|---|---|---|
| 5,197,484 | A | * | 3/1993 | Kornberg et al. | 600/567 |
| 5,336,178 | A | | 8/1994 | Kaplan et al. | |
| 5,511,895 | A | * | 4/1996 | Myers | 403/371 |
| 5,720,717 | A | | 2/1998 | D'Andrea | |
| 6,251,060 | B1 | * | 6/2001 | Hooft | A61M 37/0069 600/3 |
| 2009/0281605 | A1 | * | 11/2009 | Marnfeldt et al. | 607/116 |
| 2012/0253410 | A1 | * | 10/2012 | Taylor | A61B 17/17 606/96 |

* cited by examiner

Primary Examiner — Brian Pellegrino

(57) ABSTRACT

An apparatus for securing a marker wire relative to a lumen includes a hub to which the marker wire is secured. The hub includes a feature that secures the hub to an outer surface of the lumen. For example, the hub may include a base member secured to the marker wire and a separate fastener member which secures the hub to an outer surface of a lumen, where the base member includes a split tube segment that receives the lumen within an inner cylindrical opening. Alternatively, the hub may include a cylindrical slide lock collar member with a split tubular extension that receives the lumen within an inner cylindrical opening. Locking features may be included to help fix the two pieces of the hub in position relative to each other.

8 Claims, 6 Drawing Sheets

SECURING A MARKER WIRE

CROSS-REFERENCE TO RELATED APPLICATIONS

N/A

BACKGROUND OF THE INVENTION

The present invention is generally related to medical treatments such as interstitial Brachytherapy. Cancers and other malignant tumors are often treated by surgical resection followed by radiation therapy which targets the residual tumor margin. The radiation therapy can be administered through various methods including external-beam radiation, stereotactic radiosurgery, and permanent or temporary brachytherapy. It is often desirable during diagnosis and treatment to be able to accurately mark a subcutaneous site. For example, the site of a biopsy may be marked to facilitate a surgical procedure or delivery of medicine or radiation treatment. One device for marking a site is a marker wire. The marker wire may be a wire, sheathed wire, or tube which is introduced to the subcutaneous site via a lumen and then secured in place. It is known to use surgical tape to secure the marker wire in place. Alternatively, a feature such as a jog or kink in the marker wire may be positioned such that an interference fit is established between the marker wire and the inner surface of the lumen. However, these methods can be unreliable. For example, it is difficult to make a jog in a tube.

SUMMARY OF THE INVENTION

In accordance with an aspect of the invention, apparatus for securing a marker wire relative to a lumen comprises a hub to which the marker wire is secured. The hub includes a feature that enables the hub to be secured to an outer surface of the lumen. In one embodiment the hub includes a base member secured to the marker wire and a separate fastener member which secures the hub to an outer surface of a lumen. The base member may include a split tube segment that receives the lumen within an inner cylindrical opening. Alternatively, the hub may include a cylindrical slide lock collar member with a split tubular extension that receives the lumen within an inner cylindrical opening. Locking features may be included to help fix the two pieces of the hub in position relative to each other.

In accordance with another aspect of the invention, a method for securing a marker wire relative to a lumen comprises inserting the marker wire into a lumen that is prepositioned in subcutaneous tissue; inserting the lumen into a corresponding split tube of a hub that is affixed to the marker wire at a distal end; and creating an interference fit between the hub and the lumen.

Various embodiments of the invention have certain advantages over taping and kinking marker wire. For example, embodiments of the invention are more reliable and easily implemented than those prior art techniques. Furthermore, the likelihood of damaging the lumen is low because the force exerted by the split tube against the lumen is distributed across the length of the split tube. The likelihood of damaging the lumen is also low because the interference fit is against the outer surface of the lumen rather than the inner surface. The split tube length may also be selected such that a predetermined magnitude of variation in length of the lumen can be accommodated, e.g., a 5 mm variation in length.

DETAILED DESCRIPTION

Figure 1:
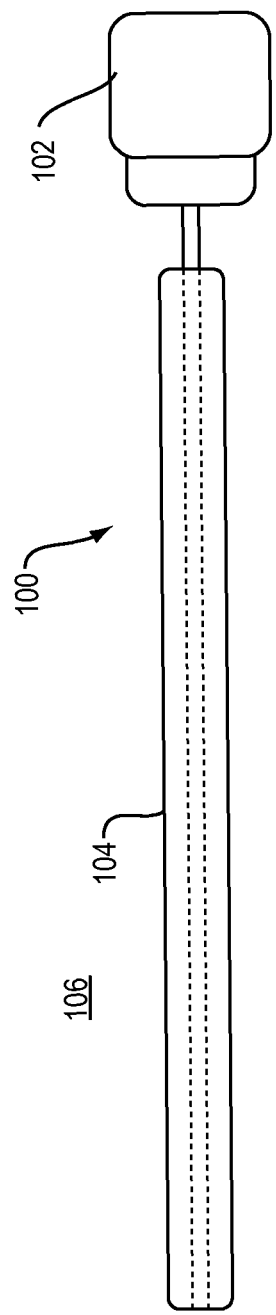
FIG. 1 illustrates a marker wire with a locking hub for securing the marker wire relative to a lumen.

FIG. 1 illustrates a marker wire 100 with a hub 102 for securing the marker wire relative to a lumen 104 disposed in subcutaneous tissue 106. The marker wire 100 is attached to the hub 102 at a distal end. For example, and without limitation, the marker wire may be welded to the hub or affixed with adhesive. Alternatively, the marker wire may be integral to the hub, e.g., formed together in a mold. The hub 102 fixes the location of the marker wire 100 relative to the lumen 104.

The marker wire 100 and hub 102 may be made from a flexible material including but not limited to plastics and metallics such as nickel titanium (Nitinol), polyurethane, nylon, Polyether Block Amide (PEBA), Low-density polyethylene (LDPE), thermoplastic polyester elastomers, or PolyEtherEther-Ketone (PEEK). In some embodiments it may be desirable for the marker wire to be imagable via various modalities based on, e.g., sonic, electromagnetic or magnetic resonance imaging techniques.

Figure 2:
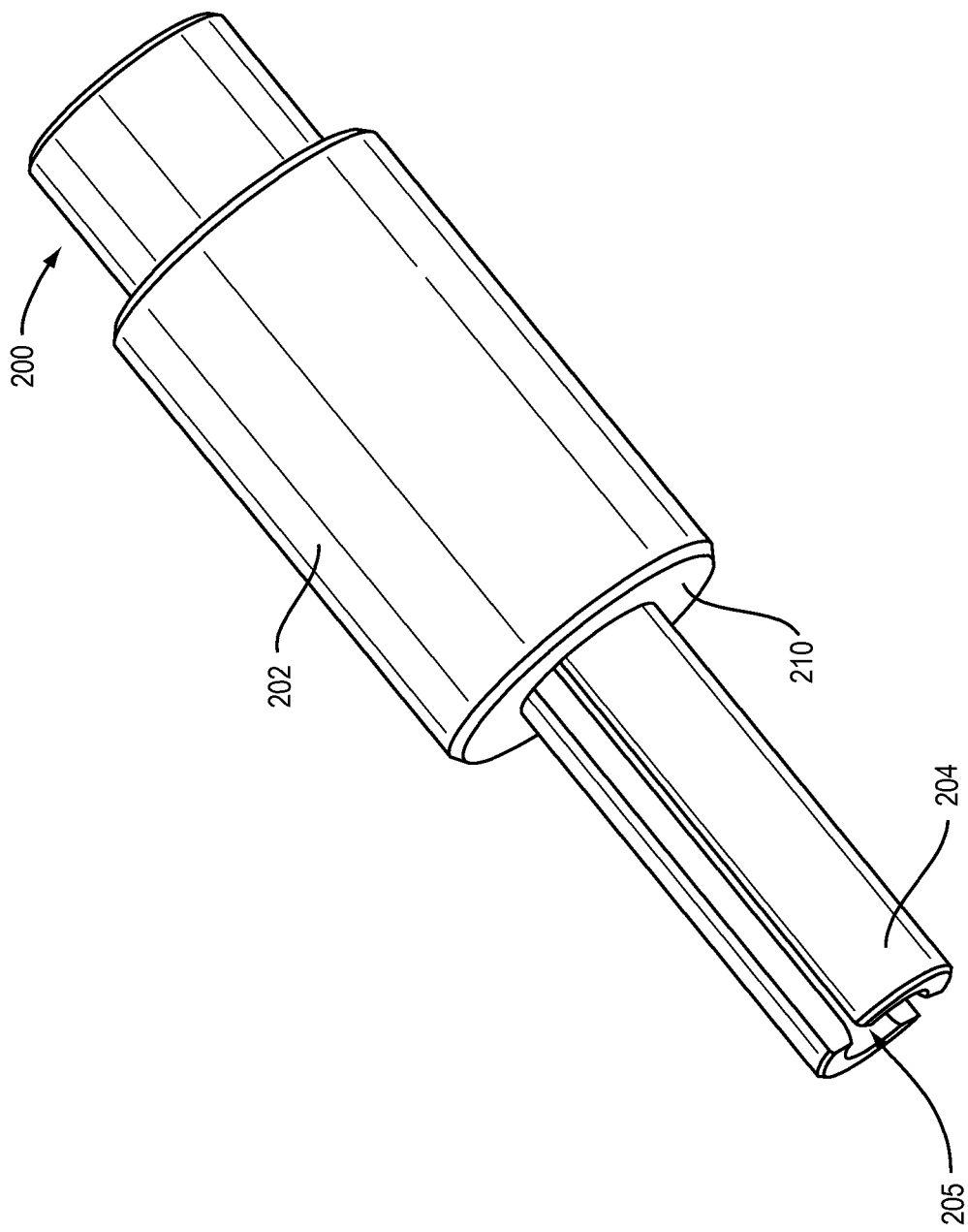
FIG. 2 illustrates a two-piece embodiment of the locking hub with a locking collar and a base member which includes a split tube.
Figure 3:
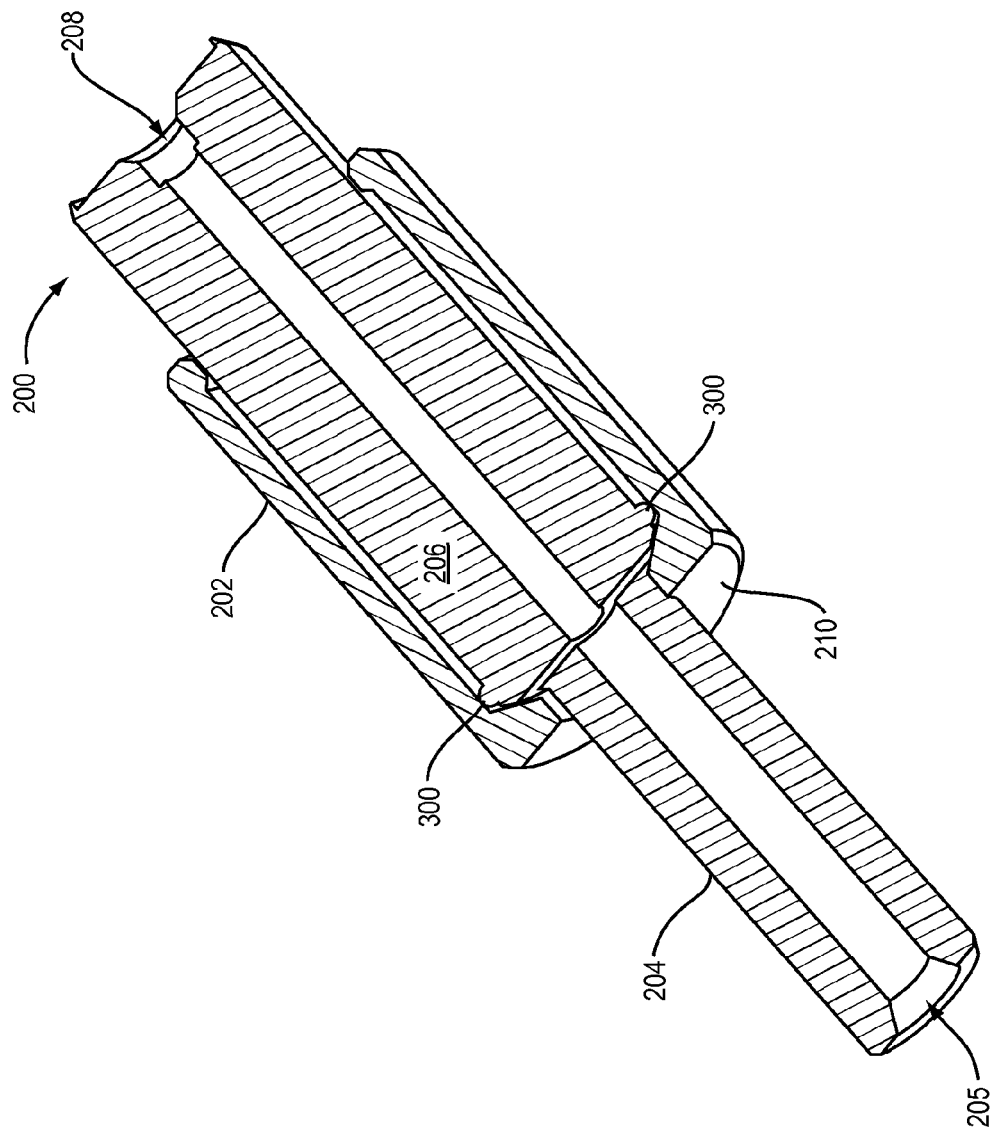
FIG. 3 is a cross-sectional view of the locking hub of FIG. 2.

Referring to FIGS. 2 and 3, in one embodiment the hub includes a base member 200 and a separate fastener member 202 that can be moved relative to each other. The fastener member 202 may be a cylindrical locking collar which fixes the location of the marker wire relative to a lumen or causes the base member to fix the location of the marker wire relative to a lumen. For example, the base member 200 may include a split tube segment 204 that receives the lumen within an inner cylindrical opening 205. The split tube segment 204 is adjacent to an unsplit segment 206 which receives the marker wire within an inner cylindrical opening 208 where the marker wire is secured to the base member 200. The unsplit segment 206 is characterized by an outer diameter that is greater than the outer diameter of the split segment 204. The fastener member 202 is characterized by an inner cylindrical opening approximately equal to the outer diameter of the unsplit segment of the base member. The cylindrical fastener member has no base at a first end and a partial base 210 at a second end. More particularly, the partial base defines a circular opening characterized by a diameter that is less than the outer diameter of the split segment 204 when the split segment is in a relaxed state, but approximately equal to the outer diameter of the split segment when the split segment is in a compressed state, i.e., when the diameter of the split segment is reduced such that the split opening partially or completely closes.

Referring to FIGS. 1 through 3, the hub is secured to a lumen by inserting the marker wire 100 into the lumen 104 and then inserting the lumen into the inner cylindrical opening of the split tube 204 when the split tube is in a relaxed state, i.e., when the partial base of the fastener member is moved slidably toward or against the unsplit segment. The cylindrical collar of the fastener member 202 is then moved slidably such that the partial base 210 of the fastener member moves away from the unsplit segment 206 of the base member. As the partial base moves along the split tube 204 it causes the split tube to decrease in diameter, thereby creating a interference fit between an inner surface of the split tube 204 and an outer surface of the lumen 104. Because the force exerted by the split tube against the lumen is against the outer surface of the lumen and distributed across the length of the split tube it is unlikely that the lumen will be damaged. The split tube length may be selected such that a predetermined magnitude of variation in length of the lumen can be accommodated, e.g., a 5 mm variation in length.

The base member 200 and a fastener member 202 may include one or more features which help lock the fastener member in position relative to the base member. In the illustrated embodiment the base member 200 includes a circular protrusion 300 disposed on the outer surface proximate to the split tube. Corresponding circular detent depressions may be disposed on the inner surface of the locking collar such that the collar is temporarily secured to the unsplit segment 206 when the partial base 210 is moved against the unsplit segment, a predetermined distance away from the unsplit segment, or both. Consequently, the hub can be locked in either a secured or unsecured state relative to the lumen. Locking the hub in the unsecured state may facilitate inserting the lumen into the split segment. Locking the hub in the secured state reduces the likelihood of unintended movement of the locking collar and provides the user with an indication that the marker wire is secured in position relative to the lumen.

Figure 4:
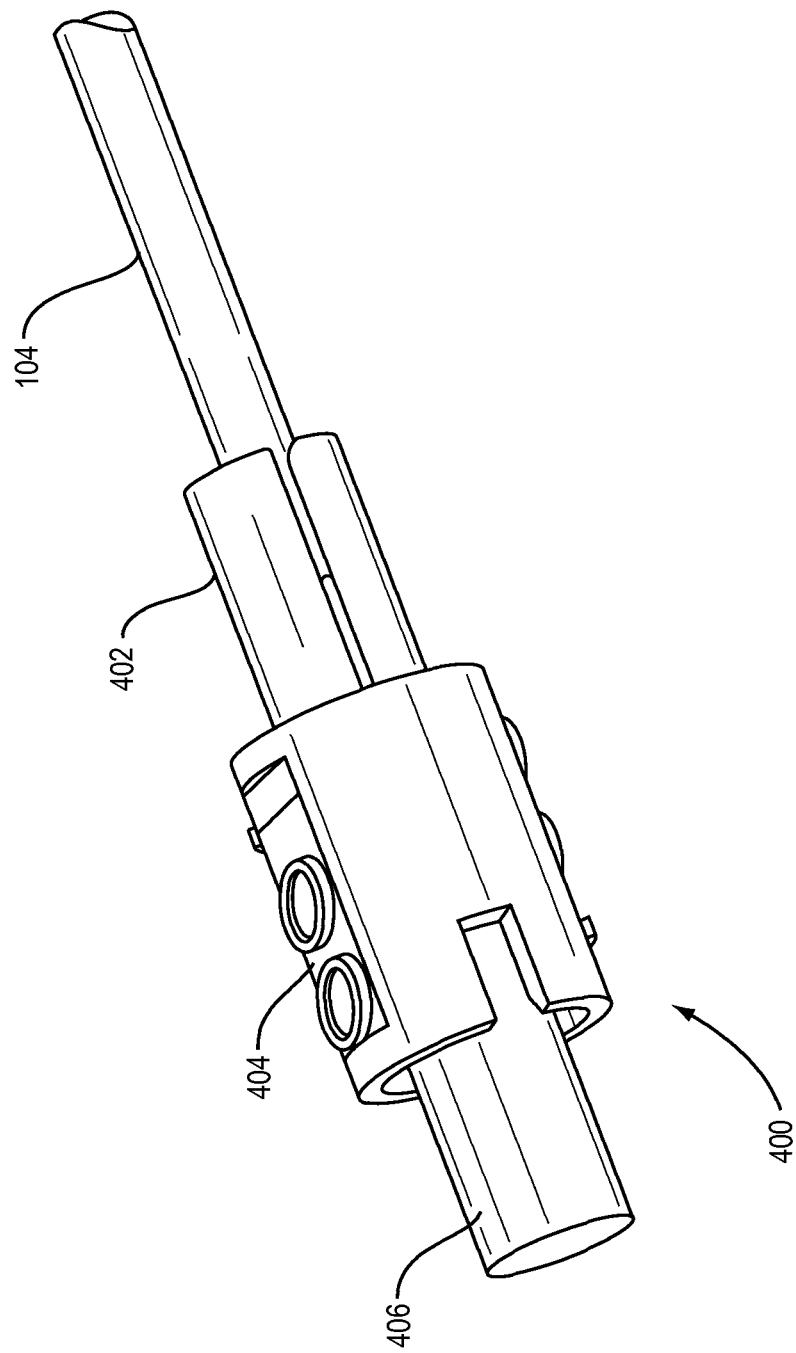
FIG. 4 illustrates an alternative embodiment of the locking hub.
Figure 5:
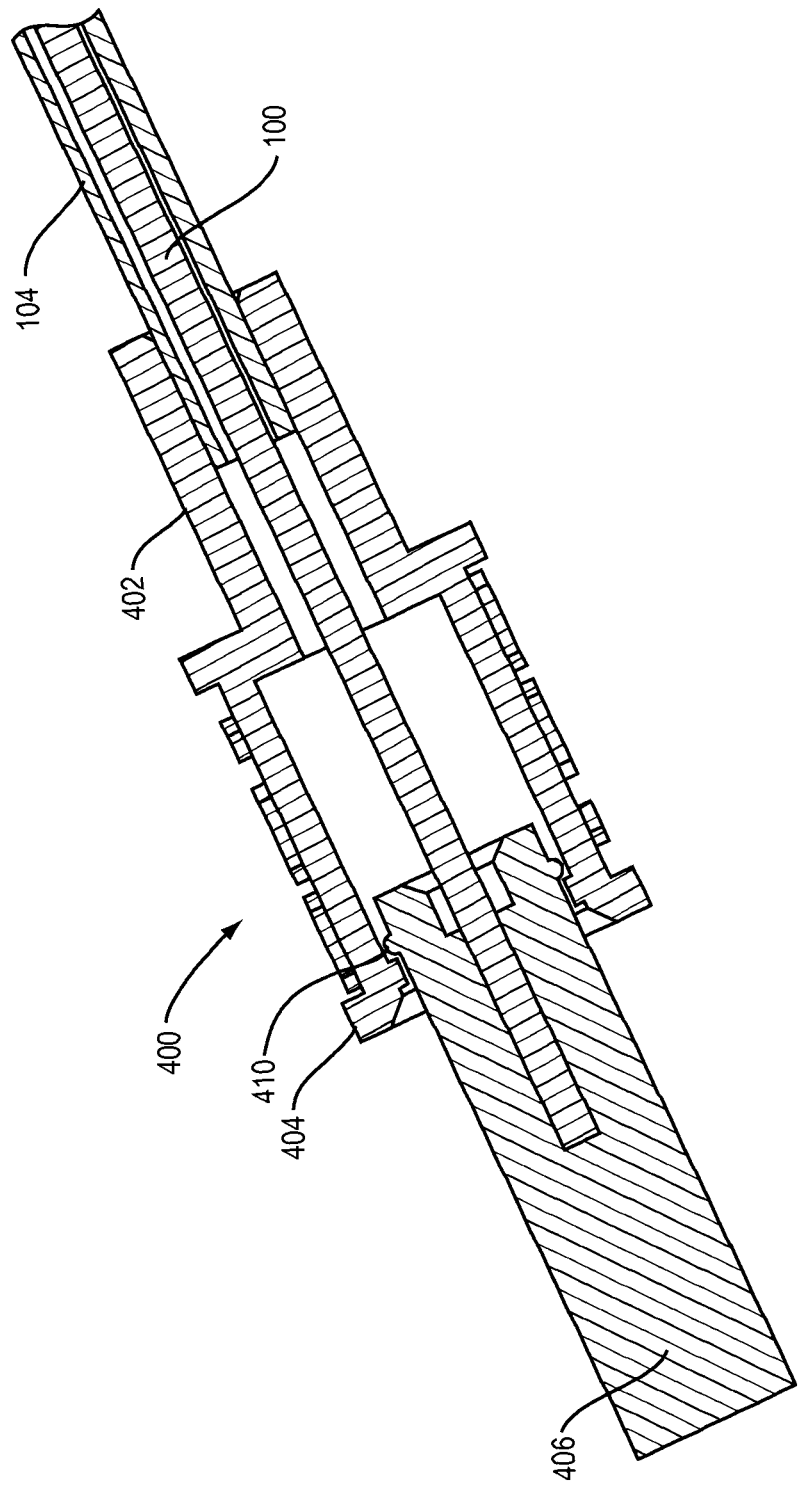
FIG. 5 is a cross-sectional view of the locking hub of FIG. 4.

An alternative embodiment is depicted in FIGS. 4 and 5. In this alternative embodiment a cylindrical slide lock collar member 400 includes a split tubular extension 402 that receives the lumen 104 within an inner cylindrical opening. The extension 402 is adjacent to an unsplit segment 404. A base member 406 receives the marker wire 100 within an inner cylindrical opening where the marker wire is secured to the base member. The unsplit segment 404 of the collar member is characterized by an inner diameter that is approximately equal to the outer diameter of the base member 406. The outer diameter of the unsplit segment is greater than the outer diameter of the extension 402. The cylindrical fastener member has no base at either end. The device is secured to the lumen by inserting the marker wire 100 into the lumen 104 and inserting the lumen into the inner cylindrical opening of the extension 402. As the collar 400 moves slidably along the lumen 104 it creates an interference fit between an inner surface of the collar and an outer surface of the lumen.

The base member and collar may include one or more locking features which help fix the collar in position relative to the base member. In the illustrated embodiment the base member includes a circular protrusion 410 disposed on the outer surface. A corresponding circular detent depression is disposed on the inner surface of the locking collar 400 such that the collar is temporarily locked to the base when the collar is moved a predetermined distance away from the base.

Figure 6:
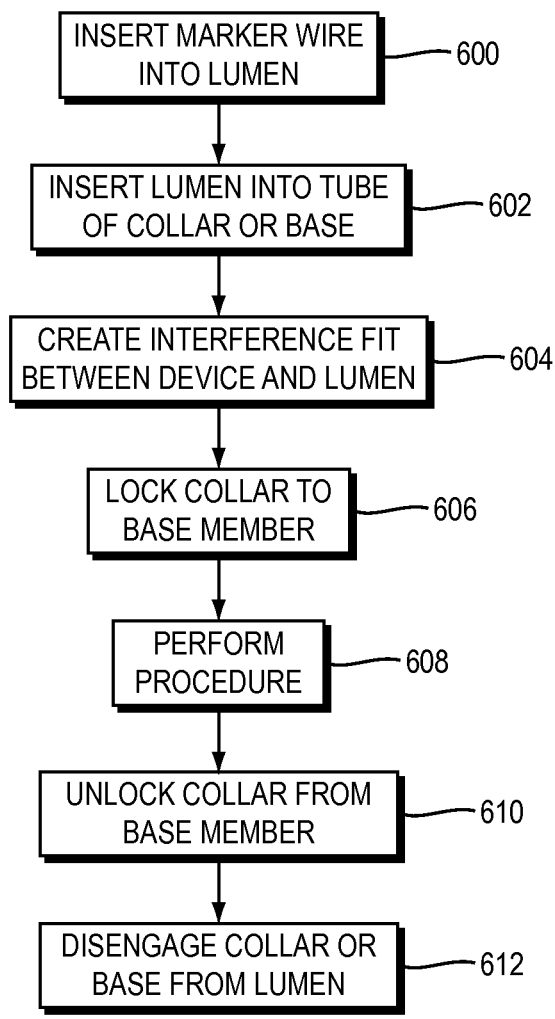
FIG. 6 is a flow diagram of a method for securing a marker wire.

FIG. 6 is a flow diagram of steps of a method for securing a marker wire. In a first step 600 the marker wire is inserted into a lumen that is prepositioned in subcutaneous tissue. The next step 602 is to insert the lumen into the corresponding tube of the collar or base of a hub that is affixed to the marker wire at a distal end. The next step 604 is to create an interference fit between the hub and the lumen. Whether the fit is between the lumen and a portion of a collar, base member or some other member will depend on which embodiment of the hub device is being utilized. If a locking feature is included then the next step 606 is to lock the collar to the base member. The procedure for which the marker wire is being used may then be performed as indicated by step 608. When the marker wire is no longer required the collar is unlocked from the base member as indicated by step 610. The collar or base is then disengaged from the lumen as indicated by step 612.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A medical imaging marking apparatus comprising:
a marker wire configured to mark a subcutaneous site;
a hub comprising:
   a base member defining an inner cylindrical opening adapted to receive the marker wire and comprising:
      a split tube segment comprising a relaxed outer diameter; and
      an unsplit tube segment adjacent the split tube segment and comprising an unsplit outer diameter greater than the relaxed outer diameter and comprising a circular protrusion on an outer surface of the unsplit tube segment; and
   a cylindrical fastener member adapted to receive the base member, wherein the cylindrical fastener member comprises:
      an end defining an opening for receiving the split tube segment, wherein the cylindrical fastener opening comprises a diameter less than the relaxed outer diameter of the split tube segment, such that receipt of the split tube segment into the cylindrical fastener opening compresses the split tube segment so as to secure the marker wire; and
      a circular detent disposed an inner surface of the cylindrical fastener member.

2. The apparatus of claim 1, wherein the circular protrusion fixes the cylindrical fastener member relative to the unsplit tube segment.

3. The apparatus of claim 1 wherein the hub is constructed from one or more of metallics such as nickel titanium (Nitinol), polyurethane, nylon, Polyether Block Amide (PEBA), Low-density polyethylene (LDPE), thermoplastic polyester elastomers, or PolyEtherEther-Ketone (PEEK).

4. The apparatus of claim 1 wherein the marker wire is imagable via at least one modality selected from a group including sonic, electromagnetic and magnetic resonance imaging techniques.

5. The apparatus of claim 1, wherein the split tube segment is slidably received in the opening defined by the end of the cylindrical fastener member.

6. The apparatus of claim 1, wherein the unsplit segment defines the inner cylindrical opening.

7. The apparatus of claim 6, wherein the marker wire is received within the inner cylindrical opening of the unsplit segment.

8. The apparatus of claim 1, wherein the cylindrical fastener member defines an inner cylindrical opening having an inner diameter approximately equal to the unsplit outer diameter.

\* \* \* \* \*